United States Patent [19]

Snowden, Jr.

[11] 4,269,604

[45] May 26, 1981

[54] METHOD FOR THE ON-SITE DETERMINATION OF THE PRESENCE OF CORROSIVE MATERIAL IN LUBRICATING OIL

[76] Inventor: James E. Snowden, Jr., 1000 Country Place Dr., #277, Houston, Tex. 77079

[21] Appl. No.: 890,055

[22] Filed: Mar. 27, 1978

Related U.S. Application Data

[63] Continuation of Ser. No. 719,591, Sep. 1, 1976, abandoned.

[51] Int. Cl.$^3$ ............................................. G01N 33/30
[52] U.S. Cl. .............................. 23/230 HC; 23/230 R; 73/64
[58] Field of Search ..................... 23/230 HC, 230 M; 324/71 R; 208/178, 179

[56] References Cited

U.S. PATENT DOCUMENTS 2,122,578  7/1938  McMaster et al. ................ 324/71 R
3,653,838  4/1972  Glass ............................... 23/230 HC

OTHER PUBLICATIONS

A.S.T.M. Standards, 1958 part 7, pp. 294–302.
A.S.T.M. Standards, 1972 part 17, pp. 227–234.
Fisher Scientific Company, TD–164, Technical Data, Dec. 1962, pp. 1–12.

Primary Examiner—Ronald Serwin
Attorney, Agent, or Firm—Arnold, White & Durkee

[57] ABSTRACT

A method of on-site determination of the presence of corrosive material in lubricating oil, comprising the steps of placing oil in a solvent of selected composition, titrating the resultant sample-solvent mixture with titrants of predetermined concentration to selected pH values, measuring the volumes of the titrants required to achieve the selected pH values, and thereafter generating signals which relate to the volumes of the titrants measured and indicating the quantity of the corrosive material in the lubricating oil.

8 Claims, No Drawings

METHOD FOR THE ON-SITE DETERMINATION OF THE PRESENCE OF CORROSIVE MATERIAL IN LUBRICATING OIL

This is a continuation of application, Ser. No. 719,591, filed Sept. 1, 1976 and now abandoned.

BACKGROUND OF THE INVENTION

1. Field of the Invention

This invention relates to a method for the on-site determination of the presence of corrosive material in lubricating oils through chemical analysis of the lubricating oil or samples thereof.

2. Description of the Prior Art

Oil used in lubricating machines or engines is subject to environmental parameters including, but not limited to, temperature, pressure and atmospheric conditions which result in chemical decomposition of the oil or degradation of the machines or engines themselves, having the effect of causing a buildup of corrosive material within the lubricating oil. This buildup requires that the lubricating oil be periodically monitored in order to determine the concentration of corrosive material present within the oil. As the concentration of corrosive material increases, the remaining usable lifetime of the oil decreases to the point where continued use of oil containing a high concentration of corrosive material is detrimental to the proper operation of the machine or engine thus necessitating removal of the lubricating oil from the machine or engine and replacement with oil containing a low concentration of corrosive material. Conversely, changing the lubricating oil too early in its operating lifetime results in significant and unnecessary expense.

Methods existing prior to the invention described herein for determining the concentration of corrosive material in lubricating oils and generally described in ASTM Procedure D-664 Potentiometric Analysis have utilized chemical procedures performed by chemists or highly skilled technicians at a laboratory, all at a great cost of time and money.

For example, machines or engines used to power oil drilling equipment utilize many gallons of lubricating oil. It is standard practice of oil manufacturers to add to the oil active anticorrosive materials which tend to inhibit the buildup of acidic corrosive materials. As the machines or engines are operated, the concentration of anticorrosive additives is depleted to the point where they fail to perform the inhibitory function, thus resulting in discernible increases in the amount of acidic corrosive material existing within the lubricating oil.

Characteristically, the lubricating oil used in drilling machines or engines has an operational lifetime dependent upon the quality of the lubricating oil, method of operation of the machines or engines and the environmental parameters to which the lubricating oil is subjected. Failure to replace lubricating oil that contains a high concentration of corrosive material causes damage to the machines or engines themselves and results in very significant repair and replacement costs.

The current methods of analyzing such oil require that samples of the oil be sent to laboratories far removed from the drilling site. Since the machines or engines used in the drilling operations are operated continuously, it is essential that information regarding the quality of the lubricating oil be transmitted to the drilling site as quickly as possible to avoid the possibility that the lubricating oil then in use within the machines or engines has exceeded its useful lifetime. As often is the case, current laboratory analyses of the lubricating oil at a place far removed from the drilling site requires a time in excess of the usable lifetime of the lubricating oil. This extended time period is due to the time involved in withdrawing a sample of the oil, sending it to a laboratory, analyzing the sample and transmitting the results back to the drilling site. Because of this time delay, the standard practice in the oil drilling industry is to replace the lubricating oil after an established operational lifetime dependent upon the operational and environmental parameters existing at the drilling site and without regard to the concentration of corrosive material within the oil. A drawback of this standard practice is that very often the oil is replaced before the concentration of corrosive materials is sufficiently high to warrant such replacement and contributes an unjustified expense to the cost of the entire drilling operation.

A feature of this invention over that of the prior art is to provide a reliable, simple and inexpensive method of on-site determination of the presence of corrosive material in lubricating oil.

A further feature of this invention is to provide a means of on-site determination of the presence of corrosive material in lubricating oil whereby the freshly removed oil, is dissolved in a solvent of selected composition with the resulting mixture being titrated to selected pH values with titrants of predetermined concentration; the volume of the titrants used to achieve the selected pH values then being measured and, subsequently, the measured volumes, together with that measured volume used to titrate a blank, being used to generate signals functionally related to the measured volumes and indicative of the quantity of the corrosive material present in the lubricating oil.

SUMMARY OF THE INVENTION

The invention is a method for on-site determination of the presence of corrosive material and active anticorrosive additive in lubricating oil. The presence of corrosive material is determined by obtaining a sample of freshly removed oil, dissolving this sample in a known volume of a solvent of selected composition, titrating the resultant sample-solvent mixture with a basic titrant of predetermined concentration to a selected basic pH value, measuring the volume of the titrant required to achieve the selected basic pH value, titrating a blank solution of substantially the same volume as the solvent to a basic pH value substantially the same as that basic pH value selected for the titration of the resultant sample-solvent mixture, and thereafter generating a signal which relates to the volume of the titrant measured, and indicates the quantity of the acidic corrosive material in said lubricating oil.

The presence of active anticorrosive additive in lubricating oil is determined by obtaining a sample of freshly removed oil, dissolving this sample in a known volume of a solvent of selected composition, titrating the resultant sample-solvent mixture with an acidic titrant of predetermined concentration to a selected acidic pH value, measuring the volume of the titrant required to achieve the selected acidic pH value, titrating a blank solution of substantially the same volume as the solvent to an acidic pH value substantially the same as that acidic pH value selected for the titrant of the resultant sample-solvent mixture, and thereafter generating a signal which relates to the volume of the titrant measure, and indicates the quantity of the active anticorrosive additive in said lubricating oil.

DESCRIPTION OF THE PREFERRED EMBODIMENT

The present invention embodies a method whereby the freshly removed oil is dissolved in a solvent of selected composition and a titrant of predetermined concentration is titrated into the resulting lubricating oil-solvent mixture until a selected pH value of the resulting mixture is achieved. As used herein, the expression "freshly removed oil" refers to oil that has been removed from a running engine or machine for only a short period of time such that a determination of the presence of corrosive material and active anticorrosive additive therein is at least approximately indicative of the amount of corrosive material and anticorrosive additive in the same oil remaining in the running engine or machine.

The titrant may be selected from a broad class of chemical compounds exhibiting acidic or basic properties. When analyzing for acidic corrosive materials, a basic titrant is used. As example, but without limitation, the basic titrant may be sodium hydroxide, potassium hydroxide, cesium hydroxide or ammonium hydroxide.

When analyzing for active anticorrosive additive, an acidic titrant is used. As further example, but without limitation, the acidic titrant may be hydrochloric acid, acetic acid, phosphoric acid, perchloric acid or formic acid.

As used herein "active anti-corrosive additive" means material added to the lubricating oil by the manufacturer which is capable of stabilizing the oil against the harmful increases of acidic corrosive materials occurring during the operation of machines or engines wherein the oil is placed.

When the presence of active anticorrosive additive of a basic nature is determined, the titration proceeds to a pH value of 2-5.

When the presence of acidic corrosive material is determined, the titration proceeds to a pH value of 8-12.

The solvent may be a combination of chemicals having the ability to dissolve the lubricating oil, corrosive material and active anticorrosive additive contained therein. As example, the solvent may be a combination of toluene, anhydrous isopropyl alcohol and water; naphthalene, ethyl alcohol and water; or xylene, methanol and water each in a ratio approximating 1:1:0.01.

In order to establish a reference point for the titration process, a measured amount of the solvent used to dissolve the lubricating oil, but containing no freshly removed oil, and known as the "blank", is titrated with the titrant to the pH value selected as the titration endpoint for titration of the lubricating oil.

The titration proceeds in two phases. In phase one, a sample of freshly removed oil is dissolved in the solvent and titrated with a basic titrant. At the completion of the titration process, the volume of the titrant used in titrating the freshly removed oil is measured. Using the measured volume, a signal is generated which is indicative of the quantity of the acidic corrosive material present in the lubricating oil. This signal is obtained thusly: the volume of the titrant used to titrate the blank is subtracted from the measured volume of the titrant used to titrate the lubricating oil; the representative volume thereby obtained is multiplied by the normality of the titrant with the resulting product further multiplied by the gram molecular weight of the basic titrant. The signal generated by this procedure is known as the "acid number".

In phase two, a separate sample of freshly removed oil, obtained at the same time as the sample used in phase one, is dissolved in the solvent and titrated with an acidic titrant. At the completion of the titration process, the volume of the titrant used in titrating the lubricating oil is measured. Using the measured volume, a signal is generated which is indicative to the quantity of the active anticorrosive material present in the lubricating oil. This signal is obtained thusly: the volume of the titrant used to titrate the blank is subtracted from the measured volume of the titration solution used to titrate the lubricating oil; the representative volume thereby obtained is multiplied by the normality of the titrant with the resulting product further multiplied by the gram molecular weight of the basic titrant. This final product is then divided by the total weight of the lubricating oil used in the analysis. The signal generated by this procedure is known as the "base number".

By testing samples of freshly removed oil at different times, an increase in the strength of the acid number represents an increase of acidic corrosive materials in the lubricating oil; a decrease in the strength of the base number represents a decrease in concentration of the active anticorrosive additive in the lubricating oil.

In order to standardize the generated signals, hereinafter referred to as the standard acid number and the standard base number, it is preferred that the method disclosed herein be first performed on unused lubricating oil. In this regard, "unused lubricating oil" means lubricating oil that has not been used, or is not currently in use, in an operating machine or engine. It is preferred that the unused lubricating oil be eventually placed in the machine or engine. It is also preferred that one or more analyses of the lubricating oil be performed on freshly removed oil after the lubricating oil has been placed within the operating environment of the machines or engines.

Whenever the subsequent analyses establish that the acid number has reached a level of equal to or greater than 2.5 to 3 over that of the standard acid number and concurrently, the base number has reached a level of equal to or less than 0.5, the lubricating oil contains sufficient acidic corrosive material to warrant replacement.

As a further example, but without limitation, the method disclosed herein may be performed as follows:

Step 1
Place 5 g of the lubricating oil into a beaker;
Step 2
Place 125 ml of the solvent, comprised of a mixture of toluene, anhydrous isopropyl alcohol and water, in the proportions 500 ml: 495 ml: 5 ml respectively, into the beaker containing the unused lubricating oil described in Step 1;
Step 3
Titrate the solution resulting from Step 2 with titrant 0.1 N alcoholic KOH until said solution achieves a pH value of 11;
Step 4
Measure the volume of titrant used in Step 3;
Step 5
Place 125 ml of the solvent defined in Step 2 into a separate beaker and titrate the solvent with the titrant defined in Step 3 to a pH value of 11;
Step 6

Measure the volume of titrant used in Step 5;

Step 7

Repeat Steps 1 and 2;

Step 8

Titrant the solution resulting from Step 7 with titrant 0.1 N alcoholic HCl until said solution achieves a pH value of 4;

Step 9

Measure the volume of titrant used in Step 8;

Step 10

Place 125 ml of the solvent defined in Step 2 into a separate beaker and titrate this solvent with the titrant defined in Step 8 to a pH value of 4;

Step 11

Measure the volume of titrant used in Step 10;

Step 12

Generate the acid number thusly:

(a) subtract the volume measured in Step 6 from that measured in Step 4;

(b) multiply the volume resulting from Step 7(a) by 56.11 g/mol times the normality of the titrant; and (c) divide the product resulting from Step 7(b) by 5 g.

Step 13

Generate the base number thusly:

(a) subtract the volume measured in Step 9 from that measured in Step 11;

(b) multiply the volume resulting from Step 13(a) by 56.11 g/mol times the normality of the titrant; and (c) divide the product resulting from Step 13(b) by 5 g.

Step 14

Repeat Steps 1 through 13 on freshly removed oil at various times and compare the signals thereby generated with the signals generated by the analyses of unused lubricating oil.

The entire procedure as outlined in Steps 1 through 14 above, and as further disclosed herein, is adapted to be carried out "on-site", that is, at the actual operational site of the machine or engine or adjacent thereto. The method does not require a laboratory or sophisticated chemical equipment, training or skills.

What is claimed is:

1. An on-site method for determining the need for replacement of lubricating oil in an engine or machine due to the buildup of acidic corrosive material and decrease of anti-corrosive additive therein, which comprises the steps of:

(a) removing a sample of oil from an engine or machine, the oil being suspected of having a buildup of acidic corrosive material therein, to provide a sample of freshly removed oil;

(b) dissolving said sample of freshly removed oil in a known volume of solvent therefor to form a solvent solution of freshly removed oil;

(c) titrating said solvent solution with a basic titrant to a preselected basic pH;

(d) titrating a blank solution of the same volume as said solvent but containing no freshly removed oil with the same titrant as used in step (c) to at least substantially the same preselected basic pH;

(e) measuring the volume of basic titrant used in each of steps (c) and (d);

(f) generating from the measurements of step (e) a signal indicative of the corrosive acidic material in the freshly removed oil;

(g) comparing the signal obtained in step (f) with a signal obtained by carrying out steps (a) through (f) on a sample of the same lubricating oil prior to its introduction into the engine or machine to obtain a comparison value indicative of acidic corrosive material buildup;

(h) removing a sample of oil from an engine or machine, the oil being suspected of having a buildup of basic corrosive material therein, to provide a sample of freshly removed oil;

(i) dissolving said sample of freshly removed oil in a known volume of solvent therefor to form a solvent solution of said freshly removed oil;

(j) titrating said solvent solution with an acidic titrant to a preselected acidic pH;

(k) titrating a blank solution of the same volume of said solvent but containing no freshly removed oil with the same titrant as used in step (j) to at least substantially the same preselected acidic pH;

(l) measuring the volume of acidic titrant used in each of steps (j) and (k);

(m) generating from the measurements of step (l) a signal indicative of the active anti-corrosive additive in the freshly removed oil;

(n) comparing the signal obtained in step (m) with a signal obtained by carrying out steps (h) through (m) on a sample of the same lubricating oil prior to its introduction into the engine or machine to obtain a comparison value indicative of the decrease of the active anti-corrosive additive in the lubricating oil; and (o) determining the time at which said comparison value of step (g) achieves a value of equal to or greater than 2.5 to 3.0 concurrent to the time which said comparison value of step (n) achieves a value of equal to or less than 0.5.

2. A method as defined in claim 1, wherein the titrant in step (c) is 0.1 N alcoholic KOH; and the pH value is 11.

3. A method as defined in claim 1, wherein the titrant in step (j) is 0.1 N alcoholic HCL and the pH value is 4.

4. A method as defined in claim 2, wherein the solvent comprises toluene, anhydrous isopropyl alcohol and water in a ratio approximating 1:1:0.01, respectively.

5. A method as defined in claim 3, wherein the solvent comprises toluene, anhydrous isopropyl alcohol and water in a ratio approximating 1:1:0.01, respectively.

6. A method as defined in claim 4, wherein the blank is 125 ml. of the solvent.

7. A method as defined in claim 5, wherein the blank is 125 ml. of the solvent.

8. A method as defined in claim 1, wherein the titrant in step (C) is 0.1 N alcoholic KOH and the pH value is 11; the titrant in step (J) is 0.1 N alcoholic HCl and the pH value is 4; the solvent comprises toluene, anhydrous isopropyl alcohol and water is a ratio approximating 1:1:0.01, respectively; and the blank is 125 ml of the solvent.

* * * * *